United States Patent [19]
Atwood et al.

[11] 3,948,605
[45] Apr. 6, 1976

[54] DILUTER FOR A KINETIC ANALYSIS APPARATUS

[75] Inventors: John G. Atwood, Redding; Lucien C. Ducret, Riverside; Charles F. De Mey II, West Redding, all of Conn.

[73] Assignee: The Perkin-Elmer Corporation, Norwalk, Conn.

[22] Filed: Aug. 22, 1974

[21] Appl. No.: 499,596

[52] U.S. Cl. ................ 23/259; 23/253 R; 73/423 A
[51] Int. Cl.² ....................... G01N 1/14; G01N 1/18
[58] Field of Search.. 23/259, 253 R, 230 A, 253 A; 73/423 R, 423 A; 74/569

[56] References Cited
UNITED STATES PATENTS

| | | | |
|---|---|---|---|
| 2,660,088 | 11/1953 | Serra | 74/569 X |
| 3,197,285 | 7/1965 | Rosen | 23/259 X |
| 3,427,135 | 2/1969 | Pelavin et al. | 23/253 R |
| 3,475,130 | 10/1969 | Baruch | 23/253 R |
| 3,552,212 | 1/1971 | Öhlin | 23/259 UX |
| 3,594,129 | 7/1971 | Jones | 23/259 X |
| 3,800,984 | 4/1974 | Phelan | 23/259 |

*Primary Examiner*—Robert M. Reese
*Attorney, Agent, or Firm*—S. A. Giarratana; F. L. Masselle; J. K. Conant

[57] ABSTRACT

A diluter for use in a kinetic analysis apparatus for picking up a serum sample from a container and diluting it into a reaction cup in which a diluter probe mounted for vertical translation and horizontal rotational motion is coupled to a sample pump with the sample pump coupled to a diluter pump and wherein the probe is caused to be lowered into a container of serum sample after which said sample pump draws into said probe a measured amount of sample whereupon said probe is raised, rotated and then lowered to a position over a reaction cup; the diluter pump is then operated to discharge said sample along with a measured amount of diluent. Vertical translation and horizontal rotation of the probe is achieved by means of a pair of coaxially disposed cylindrical cam members one of which is fixed and the other rotatable about the common axis. Cut-out portions in the cam members define respective coacting camming surfaces which are engaged by and control the vertical position of a radial probe-supporting arm as it rotates about the common axis between respective limit positions where the probe overlies the sample container and reaction cup.

7 Claims, 6 Drawing Figures

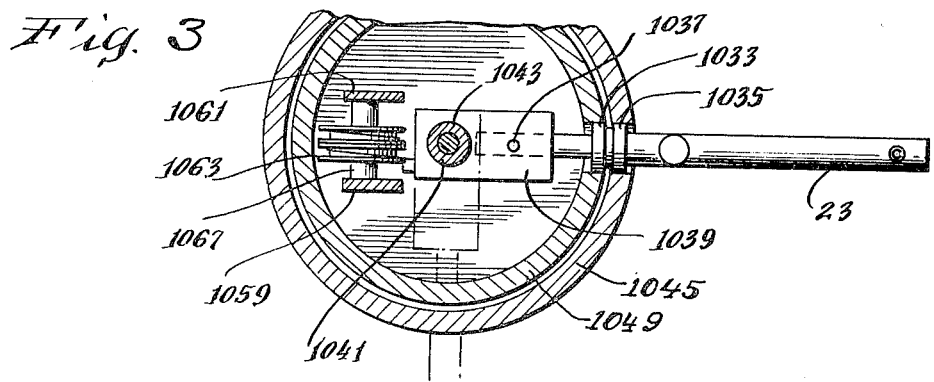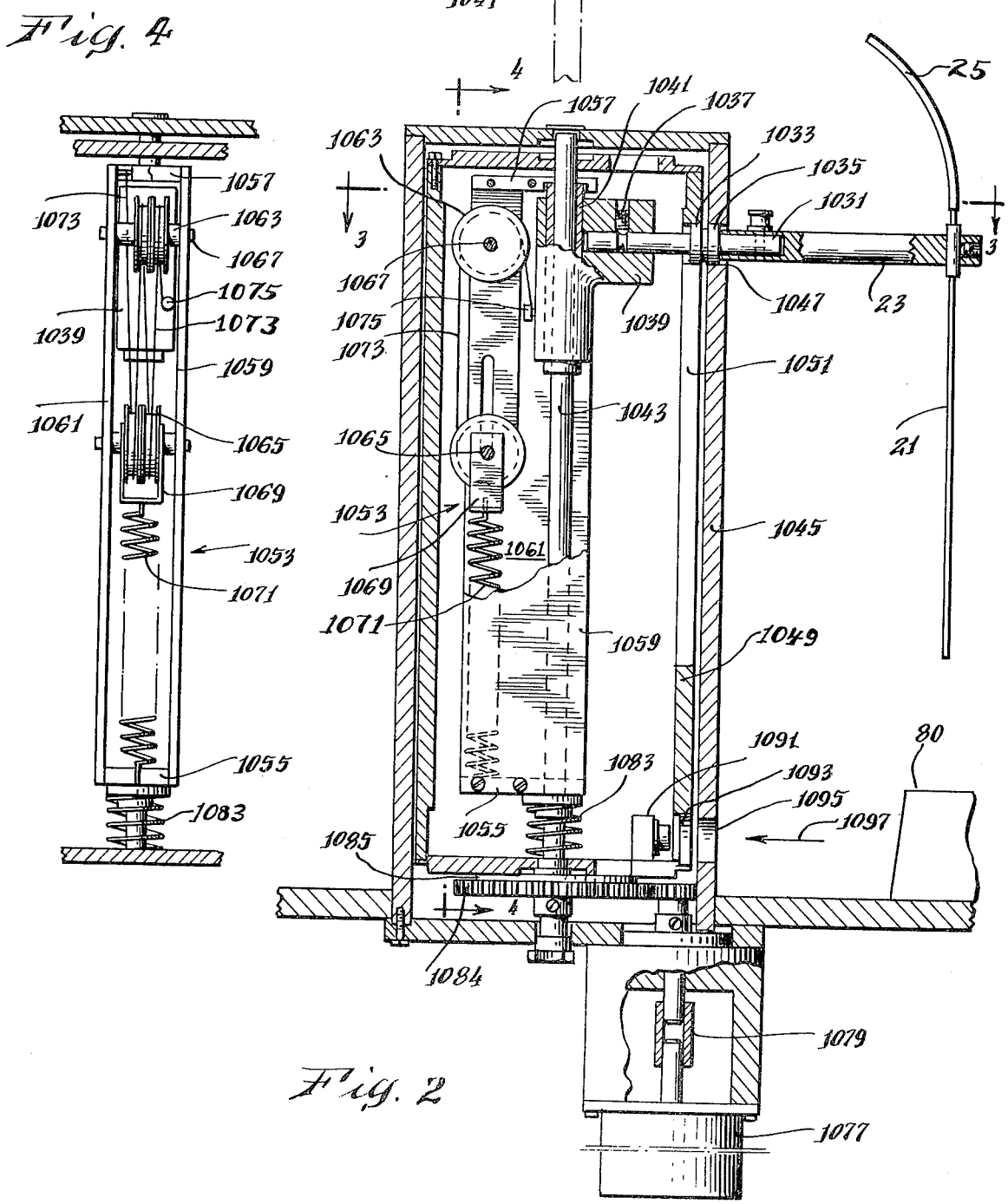

DILUTER FOR A KINETIC ANALYSIS APPARATUS

BACKGROUND OF THE INVENTION

This invention relates to analysis in general and more particularly to an improved automatic diluter for use in kinetic analysis apparatus. In an application of John S. Atwood et al, Ser. No. 594,951, filed July 10, 1975 as a continuation of now-abandoned application Ser. No. 494,602 filed on Aug. 22, 1974 the completely automatic kinetic analysis apparatus, is disclosed. In that apparatus which operates with microliter quantities, it is essential that the serum sample to be analyzed be deposited in an accurately controlled amount along with an accurately controlled amount of diluent into a reaction cup.

It is only through the ability to operate automatically with such microliter quantities that an apparatus of this nature can provide significant advantages in speed and cost over prior art apparatus using larger quantities while at the same time maintaining accuracy in excess of that previously available.

SUMMARY OF THE INVENTION

The diluter of the present invention fills the needs of such an apparatus. The diluter achieves good repeatability in metering an ultra micro sample yet operates rapidly and with very low sample carry-over in spite of the relatively low dilution ratio such as 10 to 1. This performance is achieved through a combination of a moving tubular probe and a cam driven pumping system with two pistons in two cylinders defining, respectively, a sample pump and a relatively larger volume diluter pump and a sliding valve connected to the probe by flexible tubing, the actions of the moving probe and pumps being coordinated so as to produce the following series of events:

The valve disconnects the large diluent cylinder from the probe and connects it to a diluent supply. The diluter pump piston retracts and fills the cylinder during the next several events. Meanwhile, the sample pump piston expels a small volume of diluent from the probe to form a drop at its tip.

The probe moves from its rest position to an irrigated sponge wiper, then down through the sponge wiper. After the tip of the probe has passed down through the sponge wiper which wipes off any diluent drop remaining at its tip, but before the probe reaches the sample, a sample displacing piston retracts the diluent to form a small air slug in the probe tip. After the probe has entered the sample the same sample displacing piston retracts the diluent farther so as to bring sample into the probe tip, below the air slug. The probe then rises up through the irrigated sponge wiper, which wipes off excess sample from the outside and tip of the probe. The probe moves to the container in which the diluted sample is to be prepared, and descends into it. The valve moves to connect the diluter pump cylinder to the probe and disconnect it from the diluent supply. The sample is expelled from the tip very slowly, to permit the air slug between the sample and diluent time to thoroughly scrub out the film of sample adhering to the inner walls of the probe tip.

After the sample and part of the air slug have been expelled slowly, the diluent piston moves to expel the desired amount of diluent through the tip at a more rapid flow rate to save time, and to mix sample with diluent by turbulence. After the desired volume of diluent has been expelled, the probe moves out of the reaction cup and back to its rest position. At the rest position, the diluent pump expels a substantial additional amount of diluent to a waste drain to wash out nearly all remaining sample adhering to the inner walls of the probe tip.

The wetting of the tip with diluent before each use and the wiping off of the excess liquid by the sponge wiper system permits metering volumes precisely by reducing carry-over. Formation of the air slug separating the sample and diluent in the probe tip further prevents contamination and carry-over keeping the diluent and samples separated until they are discharged into the cup. The slow expulsion of the sample followed by a rapid expulsion of diluent at the waste station further reduces carry-over.

BRIEF DESCRIPTION OF THE DRAWINGS

FIG. 2 is a sectional view illustrating the diluter probe mechanical drive.

FIG. 3 is a fragmentary sectional view along line 3—3 of FIG. 2.

FIG. 4 is a sectional view along line 4—4 of FIG. 2 illustrating a spring biasing arrangement for the diluter probe.

DETAILED DESCRIPTION OF THE PREFERRED EMBODIMENT

Table I below lists the required operation of the diluter of the present invention in an apparatus such as that of the aforementioned application. Herein, the diluter pumping is disclosed in combination with the pipetter of that apparatus.

Table I

| Preparation Unit Timing | |
|---|---|
| Elapsed Time (Seconds) | Action |
| 0.1 | Start Pipetter |
| 0.9 | 1) Stop Pipetter |
| | 2) Start diluter pump |
| 1.5 | Start diluter probe |
| 2.1 | Start Pipetter |
| 3.4 | Stop diluter pump |
| 4.0 | Stop diluter probe |
| 4.6 | Start diluter pump |
| 4.8 | Stop Pipetter |
| 6.1 | 1) Start diluter probe |
| | 2) Start Pipetter |
| | 3) Stop diluter pump |
| 7.9 | Stop Pipetter |
| 10.1 | 1) Start diluter pump |
| | 2) Check mode |
| 10.9 | 1) Stop diluter probe |
| | 2) Start table |
| 13.1 | Start Pipetter |
| 13.5 | Start diluter probe |
| 13.9 | Stop diluter pump |
| 15.4 | 1) Start diluter pump |
| | 2) Move, Go |
| 16.8 | End of Cycle |

Figure 1:
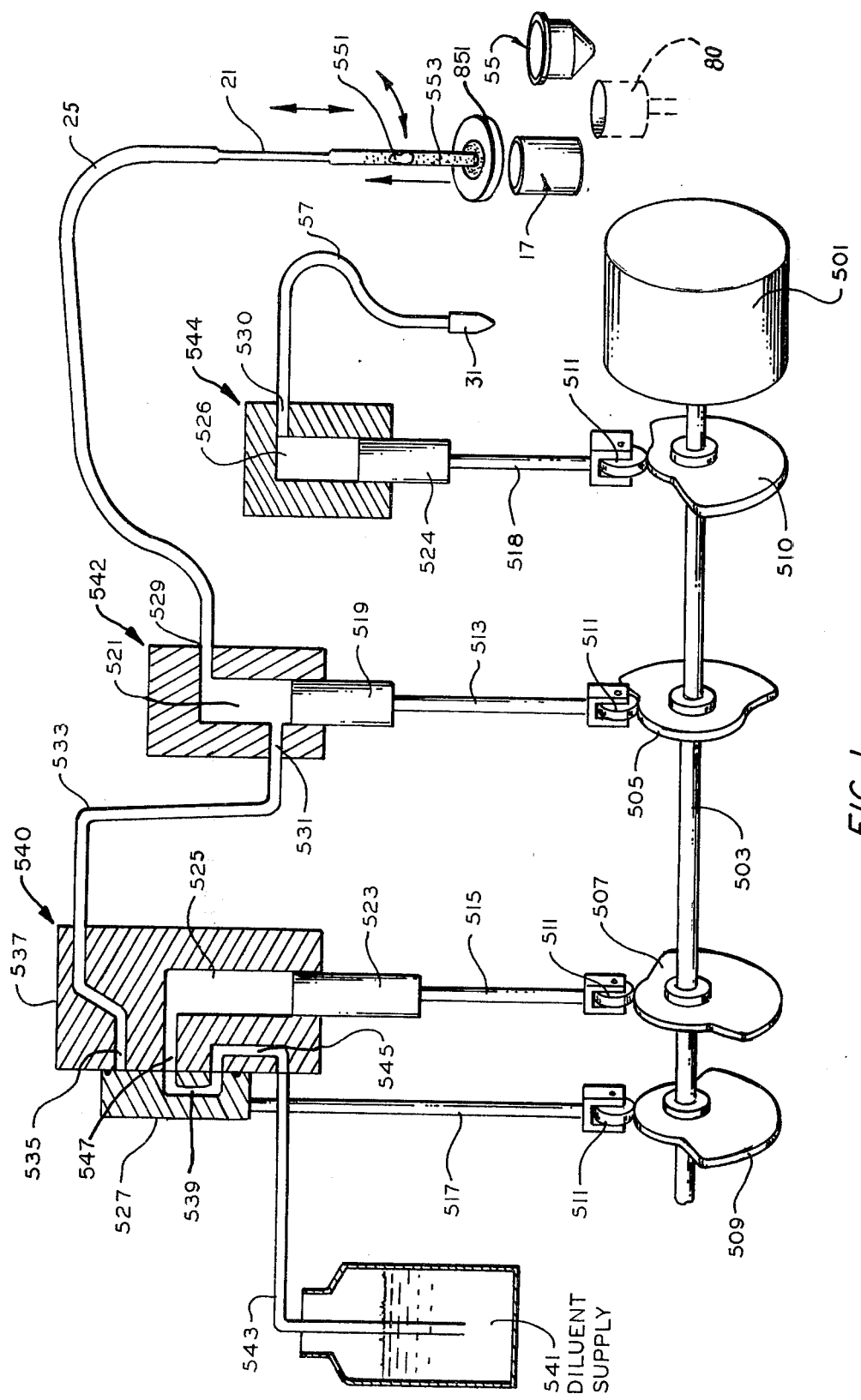
FIG. 1 is a schematic illustration of the diluter pump of the present invention combined with a pipetter pump.

FIG. 1 is a schematic perspective view of a diluter system constituting an embodiment of the present invention. The system includes a motor 501 which will be energized and controlled by a suitable circuit such as that described in the aforementioned application. Referernce should also be had to Table I above which indicates the cycles of operation. On the shaft 503 of the motor are four cams 505, 507, 509 and 510. In contact with each of the cams are respective cam followers 511 each attached respectively to pushrods 513, 515, 517 and 518. On the end of rod 515 is a piston 523 operating within a cylinder bore 525. Rod 517 has on its end a slide valve member 527. The cylinder bore 521 has a port 529 which is coupled by a flexible tube 25 also shown on FIG. 2, to a sample probe 21. Another port 531 in cylinder 521 is coupled by a conduit 533 to a passage 535 in the block 537 containing cylinder bore 525. When slide valve member 527 is in its uppermost position, passage 535 is coupled through a valve member passage 539 to a port 547 opening into cylinder 525. A container 541 filled with diluent is coupled through an appropriate conduit 543 to a further passage in block 545 which 537 is coupled to cylinder port 547 via passage 539 when slide valve member 527 is in its lowermost position as depicted in FIG. 1.

Rod 518 drives a piston 524 in a cylinder bore 526 having a port 530 which connects the bore with a flexible tube 57 connected to a pipetter 31. For ease of identification, the pump including piston 523 and cylinder 525 may hereinafter be termed diluter pump (540) the pump including piston 519 and cylinder 521 the sample pump (542) and the pump including piston 524 in bore 526 the pipetter pump for (544).

Reverting now to Table I, at time 0.1 the pipetter drive is started to move pipetter 31 into position in a reagent container, now shown. At time 0.9, the pipetter motion is stopped and diluter pump 540 started. The motor 501 rotates cam 510 causing pipetter pump piston 524 to be drawn down drawing reagent into the pipetter 31. The pipetter pump contains only air with a partial vacuum being created by the piston motion to draw the reagent into the pipetter 31. Thus, reagent is present only within the glass pipetter 31 which is interchangeable. At time 1.5, diluter probe 21 is activated its drive mechanism moving it from the resting position over a flushing station 80 to a position over a sample cup 17.

As previously explained, sample pump piston 519 expels a small volume of diluent to form a drop at the tip of probe 21. As the probe moves downwardly into sample cup 17, it passes through an irrigated sponge wiper unit 851 which wipes off any diluent droplet remaining at the probe tip. Wiper unit 851 is described in detail in the aforementioned copending application as well as in a copending application of John G. Atwood et al., Ser. No. 499,856, filed Aug. 22, 1974 and assigned to the same assignee as the present invention.

At time 2.1 the pipetter is started again to move it from the reagent container to a position over a reaction cup 55. At time 3.4, diluter pump 540 is stopped and at time 4.0 the diluter probe 21 is stopped.

At the beginning of the cycle, the piston 519 was at the top of its stroke. At time 2.1 when the pipetter drive starts to withdraw the pipetter from the reagent and move it to reaction cup 55 a flat on cam 510 of the pipetter pump 544 is reached to prevent further drawing in of reagent. Rotation of the shaft 503 continues, however, to drive the cam 505 associated with the sample pump piston 519 to cause a small air bubble 551 to be drawn into the probe 21 before it reaches the serum sample. At time 4.0, the diluter probe 21 is stopped in the serum sample and at time 4.6 the diluter pump 540 started again. At time 4.8 the motion of pipetter 31 is stopped, now in position over reaction cup 55. Restarting of sample pump 542 results in the piston 519 being moved further down in the bore 521 to draw into the probe the required amount of serum 553. During operation of the diluter system including both the sample pump and diluent pump (but excluding pipetter pump cylinder 526 and conduit 57), all conduits are continuously filled with water except for the air bubble 551 described above. Thus, as sample pump piston 519 is drawn farther down into the cylinder 521, diluent water in will be drawn from tube 25 into the cylinder and the remainder of the tube 25 will be filled with water except for the air bubble 551 and the serum sample 553. Following the time 4.8 when the pipetter is stopped, rotation of the cam 510 will drive pipetter pump piston 524 upward to discharge the reagent contained within the pipetter 31. At time 6.1, the diluter probe motion resumes the pipetter is started to return it to the reagent supply and the diluter pump is stopped. At this time, a full sample will be in probe 21.

During this beginning portion of the cycle, the valve 527 was maintained in its lowermost position as shown in FIG. 1 and the piston 523 moved from its up to its down position drawing diluent from the container 541 through conduit 543, passage 545, valve member 527 and port 547 into the cylinder 525. The diluter probe which started movement at time 6.1 is caused to raise and rotate to a position over reaction cup 55. At time 7.9, pipetter 31 stops over its reagent supply. At time 10.1 the diluter pump motor is started again causing the valve member 527 to move to the upper position so that valve passage 539 couples ports 535 and 547. Also at this time, a small amount of remaining reagent is discharged from pipetter 31 to an associated sponge (not shown). At this point, probe 21 is moving down into the reaction cup. The probe is stopped at 10.9 but diluter pump 540 is still running, cam 507 driving piston 523 upwardly. The piston 519 is now in the position shown in FIG. 1 so that diluent is pumped out of the cylinder 525 through port 547, valve passage 539, passage 535, and conduit 533 into cylinder 521 and thence through the port 529 into flexible tube 25. This results in the serum sample being pumped into reaction cup 55. Because of the greater displacement of the cylinder 525 as compared to 521, not only is the sample pumped out but a measured quantity of diluent along with it. However, diluter pump piston 523 is not moved all the way up during this cycle but is stopped in a mid stroke position. It will be understood that, at this time, the complete (except for pipetter cylinder 526 and conduit 57) system contains water. At time 13.5 the diluter probe is started again and at time 13.9 diluter pump 540 is stopped. The probe rotates until it is over the flushing station 80 and stops, whereupon, at the time 15.4, the diluter pump is restarted, piston 523 moving to the top of its stroke to rinse out the probe. Motor 501 then stops, halting diluter pump 540 with its piston 523 at the top of its stroke. This will occur approximately at the time 16.8 which is the end of the cycle. The motor is then ready to start another cycle in response to a new timer output.

Referring now to FIGS. 2, 3, and 4 which illustrate the diluter probe actuating mechanism, and first in particular to FIG. 1, diluter probe 21, is supported by an arm 23, attached using a screw connection to one end of a shaft 1031 supported in two bearings 1033 and 1035. The other end of the shaft 1031 is secured with a set screw 1037 to a boss 1039 extending radially from an essentially cylindrically-shaped member 1039 having an axial bore containing a bushing 1041 slidably and rotatably mounting member 1039 on a rod 1043.

Concentrically surrounding the rod 1043 is a fixed outer cam member 1045 of cylindrical shape continuing a slot 1047 therein forming its cam surfaces engaged by bearing 1035. A portion of slot 1047 is shown in FIG. 2; substantially the entire slot appears in FIG. 5. Located concentrically within the cylindrical cam member 1045 is an inner cylindrical cam member 1049, having a cut-out portion 1051 which defines a caming surface, shown in FIG. 6, for bearing 1039. The better caming surfaces will be described in greater detail presently in connection with FIGS. 5 and 6. Member 1039 is biased in an upward direction by a spring and pulley arrangement indicated generally as 1053 and including a bottom member 1055 mounted to the shaft 1043, a top member 1057 in contact with the bushing 1041 of member 1039 at the top of the shaft 1043 and side members 1059 and 1061 shown on FIG. 4. As illustrated on the figure the side pieces and top and bottom pieces are assembled in a conventional manner using screws. Located between the sides 1061 and 1059 are two double pulleys 1063 and 1065. Pulley 1063 is mounted on an axle 1067 passing through the sides 1059 and 1061 and is thus fixed with respect thereto. The pulley 1065 is supported within a bracket 1069 having attached to it one end of a spring 1071 which has its other end affixed to the bottom member 1055. As best appears in FIG. 2, a cable 1073 is attached to the top member 1057, runs over one side of bottom pulley 1065, then over one side of top pulley 1063, then over the other side of bottom pulley 1065 and the other side of top pulley 1063 and finally is attached to the member 1039 at a point 1075. Spring 1071 urges the pulley 1065 downward which in turn causes a lengthening of the amount of cable 1073 between the two pulleys resulting in the member 1039 being urged upwardly. Thus, the member 1039 and, concomitantly arm 23 and probe 21 are biased upwardly against the cam surfaces.

The inner cam member 1049 is rotatable and the outer cam 1045 fixed. Shaft 1043 is mounted in suitable bearing means at the top and bottom of outer cam member 1045 and is free to rotate therein. A motor 1077, through a coupling 1079, drives gear 1081 meshing with a gear 1083 attached to the shaft 1043 causing rotation thereof. However, since the member 1039 is free to rotate on shaft 1043 as is the inner cam member 1049 no further rotation takes place due simply to rotation of shaft 1043. However, a spring 1083 is provided pressing the bottom of inner cam member 1049 downwardly against a fiber clutch member 1085, so that the rotation of the gear 1084 is transmitted to the inner cam member 1049 resulting in its rotation. The manner in which rotation of the inner cam with respect to the outer cam causes the desired probe movements will be explained below in connection with FIGS. 5 and 6. However, one additional item shown on FIG. 2 should be noted. Mounted within, and at the bottom of, inner cam member 1049 is a retro-reflector 1091 aligned with an aperture 1093 in the inner cam member which registers with an aperture 1095 in outer cam member 1045 when the cam members are at the starting position. Thus, when the required sequence of events has taken place light directed along a path 1097 by a dual-optical angle sensor 80 can be used to stop the diluter sequence. For a complete description of the angle sensing system, reference may be had to the above-identified copending application, Ser. No. 499,602 or to a copending application of John G. Atwood et al., Ser. No. 499,495, filed Aug. 22, 1974 and assigned to the same assignee as the present invention.

Figure 5:
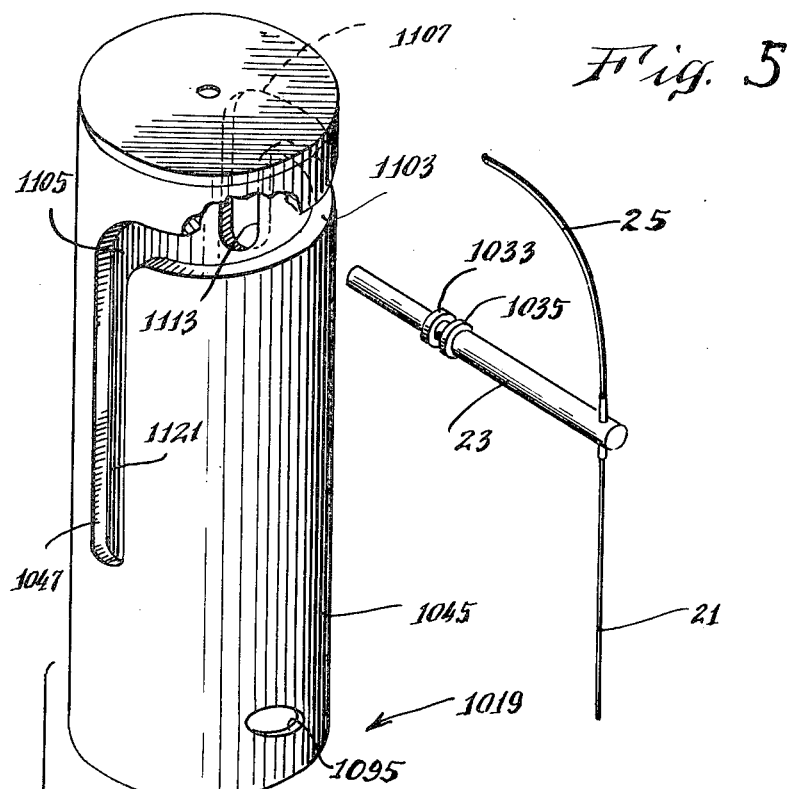
FIG. 5 is an exploded view of the cams used for controlling motion of the diluter probe.
Figure 6:
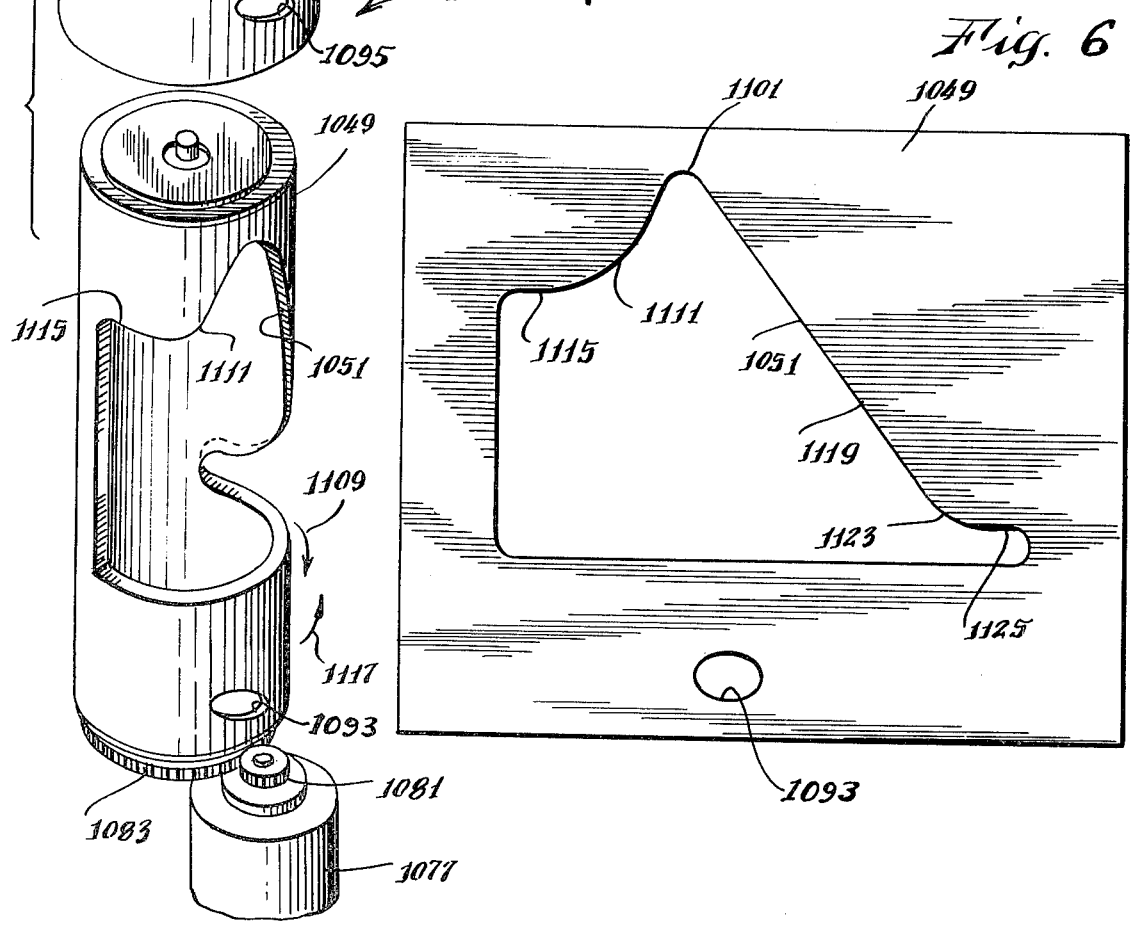
FIG. 6 is a developed view of one of the cams of FIG. 5.

FIG. 5 is an exploded view showing cam member 1045 and 1049, the probe 21, the probe arm 23 and the bearings 1033 and 1035. As noted above, outer cam member 1045 is fixed and inner cam member 1049 is rotatable by motor 1077 through gears 1081 and 1083 and the friction-clutch 1085 as described above. In the position illustrated by FIG. 5, the bearing 1033 will be in contact with inner surface 1051 at point 1101 while bearing 1035 will be riding in the horizontal portion 1103 of the cam slot 1047 in the fixed cam member 1045. The bottom horizontal surface of portion 1103 prevents movement up and down and thus between the points 1105 and 1107 the probe 21 will rotate as the inner cam member 1049 is rotated. Consider first what would occur if the inner cam 1049 were rotated in the direction of arrow 1117. The arm 23 and with it probe 21 will rotate over to point 1107. As rotation of inner cam member 1049 continues, the probe arm 23 will be pushed downward by the inner cam surface 1111 moving down in the verticle slot 1113 of the outer cam member until it reaches the bottom. At that point, bearing 1033 will be resting on the flat surface 1115 of the inner member cam. This corresponds to the position where the probe 21 is in the reaction cup 55 (FIG. 1). Rotation of the inner cam member in the direction of arrow 1109 from the position just described will result in the bearing 1033 being guided by inner cam surfaces 1115 and 1111 up to point 1101 whereupon the arm 23 will be caused to rotate to the point 1105 of the outer cam surface. At that point the cam surface portion 1119 will press on bearing 1033 causing it to move downward in the slot 1121 of the outer cam member. Bearing 1033 will move down in a linear fashion along the surface 1119 and then move slowly as it reaches the surface 1123 on inner cam member 1049 until finally it reaches the flat portion 1125 at which point it will be at the bottom of the slot 1121 and probe 21 will be positioned in a serum cup sample 17 (FIG. 1). Inner cam surfaces 1123 and 1111 are both parabolic to minimize acceleration at the points where the probe tip is moved into and out of the liquid both in sample cup 17 and reaction cup 55. Otherwise, large accelerations could cause inaccuracies in the metering of the material picked up and discharged by the probe.

Thus, an improved diluter for analysis apparatus has been shown. Although specific embodiments have been illustrated and described, it will be obvious to those skilled in the art that various modifications may be made without departing from the spirit of the invention which is intended to be limited solely by the appended claims.

What is claimed is:

1. A mechanism for moving a probe rotationally about a vertical axis between two spaced locations and translationg said probe vertically at each of said locations, comprising:
   a. a central shaft defining said vertical axis;
   b. a fixed cylindrical cam member disposed coaxially about said shaft and containing a slot defining a camming surface having two vertical portions interconnected at their upper ends by a horizontal portion;

c. a movable cylindrical cam member mounted for coaxial rotation about said shaft between angularly spaced limits and containing an opening defining a second camming surface, the vertical position of said second camming surface at said limits of rotation coinciding respectively with the lower ends of said vertical portions of the first camming surface, the second camming surface at a location intermediate said limits of rotation having a vertical position which coincides with said horizontal portion of the first camming surface, said second camming surface having smooth transitional portions between said vertical positions and said intermediate location;

d. a radial arm mounted for vertical and rotational displacement on said central shaft and extending through the slot and opening of the fixed and movable cam members, respectively, and operatively engaging said camming surfaces;

e. means on the distal end of said radial arm for mounting a probe; and f. means to rotate said movable cam member.

2. A mechanism according to claim 1 further including means to spring load said arm in a downward direction.

3. A mechanism according to claim 1 wherein said drive means comprise:

a. a motor having a first gear fixed to its shaft;

b. a second gear, engaging said first gear, and fixed to said central shaft; and c. a clutch member coupling said second gear and said inner cam member.

4. A mechanism as in claim 1 wherein said transitional portions of the second camming surface are at least partially in parabolic form.

5. A mechanism according to claim 1, further including bearing means on said respective cam surfaces.

6. Apparatus for diluting and conveying a sample from a sample container to a reaction cup comprising a probe moving mechanism according to claim 1 and further comprising:

a. a positive displacement diluter pump;

b. a positive displacement sample pump;

c. a flexible tube for connecting said sample pump to a sample probe in said probe mounting means;

d. a valve for alternately coupling said diluter pump to a source of diluent and to said sample pump; and e. means for driving said diluter pump, sample pump, and valve.

7. Apparatus for diluting and conveying a sample from a sample container to a reaction cup comprising a probe moving mechanism according to claim 1 and including a wiping unit for the probe disposed in one of the vertical translating paths of the probe and above the sample container.

* * * * *